US010115040B2

(12) United States Patent
Brauer (10) Patent No.: US 10,115,040 B2
(45) Date of Patent: Oct. 30, 2018

(54) CONVOLUTIONAL NEURAL NETWORK-BASED MODE SELECTION AND DEFECT CLASSIFICATION FOR IMAGE FUSION

(71) Applicant: KLA-Tencor Corporation, Milpitas, CA (US)

(72) Inventor: Bjorn Brauer, Beaverton, OR (US)

(73) Assignee: KLA-Tencor Corporation, Milpitas, CA (US)

(*) Notice: Subject to any disclaimer, the term of this patent is extended or adjusted under 35 U.S.C. 154(b) by 55 days.

(21) Appl. No.: 15/371,882

(22) Filed: Dec. 7, 2016

(65) Prior Publication Data

US 2018/0075594 A1     Mar. 15, 2018

Related U.S. Application Data

(60) Provisional application No. 62/394,744, filed on Sep. 14, 2016.

(51) Int. Cl.
*G06K 9/66* (2006.01)
*G06T 7/00* (2017.01)
(Continued)

(52) U.S. Cl.
CPC .............. *G06K 9/66* (2013.01); *G01N 21/88* (2013.01); *G06K 9/6267* (2013.01); *G06T 7/001* (2013.01);
(Continued)

(58) Field of Classification Search
CPC .................. G06T 7/0004; G06T 11/60; G06T 2207/20221; G06T 2207/30148; G06K 9/66; G06K 9/6267
See application file for complete search history.

(56) References Cited

U.S. PATENT DOCUMENTS

2005/0002560 A1* 1/2005 Yamamoto ........... G06K 9/3233
                                                                     382/156
2008/0167829 A1    7/2008 Park et al.
(Continued)

FOREIGN PATENT DOCUMENTS

JP          5509581 B2       6/2014

OTHER PUBLICATIONS

ISA/KR, International Search Report for PCT/US2017/051405 dated Nov. 30, 2017.

*Primary Examiner* — Bhavesh Mehta
*Assistant Examiner* — Menatoallah Youssef
(74) *Attorney, Agent, or Firm* — Hodgson Russ LLP (57) ABSTRACT

Systems and methods for classifying defects using hot scans and convolutional neural networks (CNNs) are disclosed. Primary scanning modes are identified by a processor and a hot scan of a wafer is performed. Defects of interest and nuisance data are selected and images of those areas are captured usa7ing one or more secondary scanning modes. Image sets are collected and divided into subsets. CNNs are trained using the image subsets. An ideal secondary scanning mode is determined and a final hot scan is performed. Defects are filtered and classified according to the final hot scan and the ideal secondary scanning mode. Disclosed systems for classifying defects utilize image data acquisition subsystems such as a scanning electron microscope as well as processors and electronic databases.

19 Claims, 4 Drawing Sheets

(51) Int. Cl.
*G01N 21/88* (2006.01)
*G06K 9/62* (2006.01)
(52) U.S. Cl.
CPC .............. *G06T 2207/20084* (2013.01); *G06T 2207/30148* (2013.01)

(56) References Cited

U.S. PATENT DOCUMENTS

| | | |
|---|---|---|
| 2010/0188657 A1 | 7/2010 | Chen et al. |
| 2011/0276935 A1* | 11/2011 | Fouquet ................ G06T 7/0006 716/112 |
| 2011/0310388 A1 | 12/2011 | Hill et al. |
| 2015/0324965 A1 | 11/2015 | Kulkarni |

* cited by examiner

CONVOLUTIONAL NEURAL NETWORK-BASED MODE SELECTION AND DEFECT CLASSIFICATION FOR IMAGE FUSION

CROSS-REFERENCE TO RELATED APPLICATIONS

This application claims priority to U.S. Provisional Application No. 62/394,744, filed on Sep. 14, 2016, the disclosure of which is incorporated herein by reference.

FIELD OF THE DISCLOSURE

The present disclosure relates to defect detection.

BACKGROUND OF THE DISCLOSURE

Fabricating semiconductor devices such as logic and memory devices typically includes processing a substrate such as a semiconductor wafer using a large number of semiconductor fabrication processes to form various features and multiple levels of the semiconductor devices. For example, lithography is a semiconductor fabrication process that involves transferring a pattern from a reticle to a resist arranged on a semiconductor wafer. Additional examples of semiconductor fabrication processes include, but are not limited to, chemical-mechanical polishing (CMP), etch, deposition, and ion implantation. Multiple semiconductor devices may be fabricated in an arrangement on a single semiconductor wafer and then separated into individual semiconductor devices.

Inspection processes are used at various steps during a semiconductor manufacturing process to detect defects on wafers to promote higher yield in the manufacturing process and thus higher profits. Inspection has always been an important part of fabricating semiconductor devices such as ICs. However, as the dimensions of semiconductor devices decrease, inspection becomes even more important to the successful manufacture of acceptable semiconductor devices because smaller defects can cause the devices to fail. For instance, as the dimensions of semiconductor devices decrease, detection of defects of decreasing size has become necessary since even relatively small defects may cause unwanted aberrations in the semiconductor devices.

As design rules shrink, however, semiconductor manufacturing processes may be operating closer to the limitation on the performance capability of the processes. In addition, smaller defects can have an impact on the electrical parameters of the device as the design rules shrink, which drives more sensitive inspections. Therefore, as design rules shrink, the population of potentially yield relevant defects detected by inspection grows dramatically, and the population of nuisance defects detected by inspection also increases dramatically. Therefore, more and more defects may be detected on the wafers, and correcting the processes to eliminate all of the defects may be difficult and expensive. As such, determining which of the defects actually have an effect on the electrical parameters of the devices and the yield may allow process control methods to be focused on those defects while largely ignoring others. Furthermore, at smaller design rules, process induced failures may, in some cases, tend to be systematic. That is, process induced failures tend to fail at predetermined design patterns often repeated many times within the design Elimination of spatially systematic, electrically relevant defects is important because eliminating such defects can have a significant overall impact on yield. Whether or not defects will affect device parameters and yield often cannot be determined from the inspection, review, and analysis processes described above since these processes may not be able to determine the position of the defect with respect to the electrical design.

One method to detect defects is to use computer vision. In computer vision, image fusion is the process of combining relevant information from two or more images into a single image. The resulting image should be more informative than any of the input images. Image fusion may use two or more different optical modes to differentiate between a defect of interest and a nuisance (i.e., noise). Finding the right mode pair for image fusion is very complicated and time-consuming. Prior art methods are solely attribute-based, for example dependent on energy or magnitude.

Tests show the simple attribute-based image fusion is not performing well. One particular source of error is that the images of the two modes have to be perfectly aligned to each other to perform the image correlation properly.

BRIEF SUMMARY OF THE DISCLOSURE

One embodiment of the present disclose can be described as a method for classifying defects. The method comprises identifying a primary scanning mode. The primary scanning mode may be identified using a processor. The primary scanning mode may be identified by running a hot scan to detect a defect.

The method further comprises performing a first hot scan using the identified primary scanning mode. The first hot scan may be performed using an image data acquisition subsystem. The method further comprises selecting a plurality of defects of interest and nuisance data in the first hot scan. One or more additional scans may be performed using one or more secondary scanning modes. The one or more secondary scanning modes may deviate from the primary scanning mode based on focus offset, aperture, spectrum, and/or polarization or any combination thereof. Each additional scan may use a different secondary scanning mode.

The method further comprises using the processor to collect one or more image sets. Each image set comprises a primary scanning mode image and one or more secondary scanning mode images. The primary scanning mode image and the one or more secondary scanning mode images correspond to a selected defect of interest or nuisance data.

In one embodiment, the input to the CNN is six images per selected defect of interest and nuisance data. The images may be 32×32 pixels in size. The six images may comprise a test image, a reference image, and a difference image for the primary scanning mode and a test image, a reference image, and a difference image for one of the secondary scanning modes. The input images may be processed through one or more rectified linear unit layers. The rectified linear unit layer may utilize one or more filters. One or more pooling layers may be utilized. The end result may be a fully connected layer.

The method further comprises dividing each collected image set into a first image subset and a second image subset. The processor trains a convolutional neural network (CNN) for each pair of primary scanning mode and secondary scanning mode. The training is performed using the first image subset. In one embodiment, training the CNN includes using transfer learning to create hyperparameters for each CNN.

The method further comprises determining an ideal secondary scanning mode, by applying each CNN to the corresponding second image subset. Each CNN may be evaluated based on the separation between the plurality of defects of interest and nuisance data. A final hot scan is performed, using the image data acquisition subsystem and the ideal secondary scanning mode.

The method further comprises classifying defects from the final hot scan by using the CNN corresponding to the ideal secondary scanning mode to filter out nuisance data in the final hot scan.

Another embodiment of the present disclosure may be described as a system for classifying defects. The system may comprise an image data acquisition subsystem and a processor in electronic communication with the image data acquisition subsystem. The processor is configured to identify a primary scanning mode; instruct the image data acquisition subsystem to return a first hot scan using the identified primary scanning mode; identify a plurality of defects of interest and nuisance data in the returned first hot scan; instruct the image data acquisition subsystem to return one or more scans using one or more secondary scanning modes; collect one or more image sets, each image set comprising a primary scanning mode image and one or more secondary scanning mode images corresponding to a selected defect of interest or nuisance data; divide each collected image set into a first image subset and a second image subset; train, for each pair of primary scanning mode and secondary scanning mode, a convolutional neural network (CNN) with the corresponding first image subset; determine an ideal secondary scanning mode by applying each CNN to the corresponding second image subset; instruct the image data acquisition subsystem to return a final hot scan using the ideal secondary scanning mode; and classify defects from the final hot scan by using the CNN corresponding to the ideal secondary scanning mode to filter out nuisance data in the final hot scan.

In one embodiment, the system may further comprise a database in electronic communication with the processor and the image data acquisition subsystem. The database may be configured to store classified defects from the final hot scan. The database may also be configured to store one or more CNNs.

DESCRIPTION OF THE DRAWINGS

For a fuller understanding of the nature and objects of the disclosure, reference should be made to the following detailed description taken in conjunction with the accompanying drawings, in which.

DETAILED DESCRIPTION OF THE DISCLOSURE

Although claimed subject matter will be described in terms of certain embodiments, other embodiments, including embodiments that do not provide all of the benefits and features set forth herein, are also within the scope of this disclosure. Various structural, logical, process step, and electronic changes may be made without departing from the scope of the disclosure. Accordingly, the scope of the disclosure is defined only by reference to the appended claims.

As used herein, the term "wafer" generally refers to substrates formed of a semiconductor or non-semiconductor material. Examples of such a semiconductor or non-semiconductor material include, but are not limited to, monocrystalline silicon, gallium arsenide, and indium phosphide. Such substrates may be commonly found and/or processed in semiconductor fabrication facilities.

A wafer may include one or more layers formed upon a substrate. For example, such layers may include, but are not limited to, a resist, a dielectric material, and a conductive material. Many different types of such layers are known in the art, and the term wafer as used herein is intended to encompass a wafer including all types of such layers.

One or more layers formed on a wafer may be patterned or unpatterned. For example, a wafer may include a plurality of dies, each having repeatable patterned features. Formation and processing of such layers of material may ultimately result in completed devices. Many different types of devices such as integrated circuits (ICs) may be formed on a wafer, and the term wafer as used herein is intended to encompass a wafer on which any type of device known in the art is being fabricated. As used herein, the term "chip" may comprise a collection of ICs designed for a particular purpose.

Although embodiments are described herein with respect to wafers, it is to be understood that the embodiments may be used for another specimen such as a reticle, which may also be commonly referred to as a mask or a photomask. Many different types of reticles are known in the art, and the terms "reticle," "mask," and "photomask" as used herein are intended to encompass all types of reticles known in the art.

Detecting defects on a wafer may involve using one or more optics modes including performing a hot scan on the wafer using the one or more optics modes and one or more defect detection algorithms A "hot scan" generally refers to a scan/inspection of a wafer performed to detect defects on the wafer by applying relatively aggressive detection settings (e.g., thresholds substantially close to the noise floor). In this manner, the hot scan may be performed to collect inspection data about the wafer that will be used for the tuning process (optics selection and algorithm tuning). The goal of the hot scan is to detect a representative sample of all defect and nuisance types on the wafer in the selected mode(s).

Embodiments described herein may include multiple hot scans, for example, one hot scan for optics selection and another for parameter tuning. The hot scan performed for parameter selection may be performed using optical mode(s) that were selected for wafer inspection. Selecting the optical mode(s) may include optics selection with overall scoring, which automatically calculates a single number that specifies how "good" a mode or combination of optics modes is at finding DOI while suppressing nuisance for a given set of defects. This eliminates the work of manually comparing the signal-to-noise ratio defect by defect across many modes and significantly reduces the optics selection time.

Embodiments described herein may utilize a set of processor nodes is configured to generate an image of the wafer using the image data stored in the arrays of the storage media and at least one additional source of data for the wafer. In this manner, the set of processor nodes may be configured to perform multi-channel image fusion. The additional source(s) of data for the wafer may include any information that is available at the time of image fusion. Such data sources may include, but are not limited to, design data, a die context map generated offline using design layout, a die context map generated offline from image(s), defect detection results, defect detection results generated using image data generated by different detection channels of an inspection system, image data generated by multiple (different) scans of the wafer (e.g., multiple scans performed using different imaging modes of the inspection system), information about a reticle used to print patterns on the wafer, etc.

Image fusion may not include simply overlaying multiple sources of data (although such overlay may also be performed by the embodiments described herein). Instead, image fusion may include combining multiple sources of data to generate a composite image. Image fusion may also be performed as described in commonly owned U.S. patent application Ser. No. 12/359,476 by Chen et al, filed Jan. 26, 2009, published as U.S. Patent Application Publication No. 2010/0188657 on Jul. 29, 2010 which is incorporated by reference. Furthermore, the set of processor nodes may be configured to detect defects using the images generated by image fusion.

Embodiments of the present disclosure use convolutional neural networks to find the best mode pair for image fusion. In one embodiment, the present disclosure utilizes complex methods for accurate alignment. For example, by aligning an optical patch image to a rendered design clip which allows embodiments of the present disclosure to predict with very high accuracy where a certain optical patch image is located in a design space. There are many ways to render wireframe designs into a gray-level image. Rendering techniques may involve passing design frames through optical simulation processes that take into account various optical components of the inspection tool and fiscal wafer properties. Optical components may include numerical aperture of the objective lens, wavelength of light used for inspection, optical apertures in illumination, and light collection paths. Other optical components may be used. Wafer properties such as material used for current and previous design layers, process layer thickness, and designs from current or previous layers may be used. With such information simulation system solves complex differential equations and achieves numerical close form solutions to render a design to obtain gray-level images. Embodiments of the present disclosure may use CNNs to classify the defects from an image fusion hot scan and to filter out noise or other nuisance data.

In addition, conventional machine learning approaches (such as supervised learning) can be used to find the best image fusion modes based on their attributes. A secondary mode in image fusion may be used to generate attributes of the defects found by the primary mode. Machine learning techniques may be used on the secondary mode and the primary mode to find which attributes best separate the defect of interest and noise or other nuisance data.

Embodiments of the present disclosure may achieve better mode selection and improve the separation between the defect of interest and noise or other nuisance data. Embodiments of the present disclosure may use all the information in the scan and difference images, not just some derived attributes to thrive a best mode pair for image fusion. In addition, the CNN may be used for defect classification during runtime.

The present disclosure may be described as a method 100 for classifying defects, for example defects on a wafer. A flowchart illustrating method 100 can be seen in FIG. 1. The method 100 may comprise identifying 101, using a processor, a primary scanning mode. As used herein, a processor may be a single processing unit or a plurality of processing units networked together. In some embodiments, the processor may be located in one or more physical locations. In other embodiments, a cloud-based processor or processors may be used.

Figure 1:
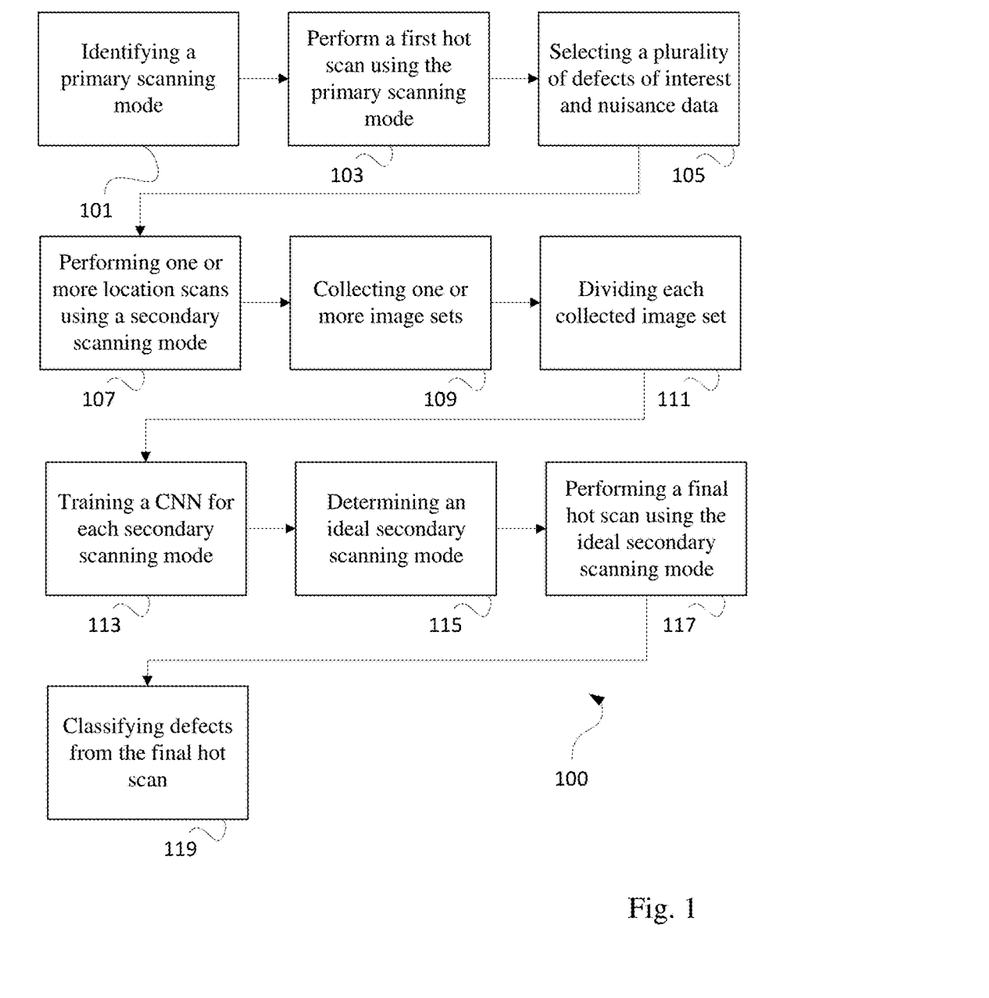
FIG. 1 is a flowchart illustrating one embodiment of the present disclosure.

A primary scanning mode may refer to parameters used by an image data acquisition subsystem. The primary scanning mode may be predetermined, for example, for a particular wafer or manufacturing process. In some embodiments, the primary scanning mode may be stored on an electronic storage device, such as a hard drive or a network drive.

The primary scanning mode may be identified 101 by searching a database to determine which primary scanning mode is appropriate for a particular application. In another embodiment, the primary scanning mode may be identified 101 based on previously run scans or images. In some embodiments, the primary scanning mode may be identified 101 based on estimated scanning parameters that have been successful in other contexts. In one embodiment, the primary scanning mode is identified by running a hot scan to detect a defect.

The method 100 may further comprise performing 103 a first hot scan using the identified primary scanning mode. The first hot scan may be performed 103 using an image data acquisition subsystem, an example of which is described below. The first hot scan may be performed 103 through instructions from the processor. The processor may be configured to send the image data acquisition subsystem parameters corresponding to the identified primary scanning mode. The processor may also be configured to receive data from the image data acquisition subsystem in response to the processor's instructions to perform 103 the first hot scan.

The method 100 may further comprise selecting 105 a plurality of defects of interest and nuisance data in the first hot scan. The processor may select 105 one or more defects of interest in the first hot scan using a variety of defect analysis tools and defect scanning methods. As used herein, nuisance data may also be referred to as noise or noise data. The nuisance data corresponds to data that may indicate an area of interest where no defect is present. Nuisance data may also refer to portions of a scan that cannot be discerned to be defect of interest or a non-defect. The processor may select 105 a plurality of defects of interest and nuisance data that is a subset of the total defects of interest and nuisance data. For example, the processor may select 105 fewer defects of interest that are present in the first hot scan.

The method 100 may further comprise performing 107 one or more additional scans using one or more secondary scanning modes. In one embodiment, the one or more additional scans may be performed 107 using the same image data acquisition subsystem. In other embodiments, the one or more additional scans may be performed 107 using a different image data acquisition subsystem. For example, a different image data acquisition subsystem may be capable of performing 107 a scan with different parameters than the initial image data acquisition subsystem.

The one or more additional scans may refer to scans that are performed 107 using different scanning parameters. Scans may be performed 107 at different speeds, distances, aperture, focus offset, spectrum, polarization, etc. Multiple scans may be performed 107, for example, using various scanning parameters. In this way, a plurality of additional scans may be performed 107, each scan collecting image data using a different set of scanning parameters. The collected image data may be associated with the same locations as the selected defects of interest and nuisance data in the first hot scan. In one embodiment, the additional scans may be performed 107 only in locations corresponding to the selected 105 plurality of defects of interest and nuisance data.

The method 100 may further comprise collecting 109 one or more image sets for each of the one or more secondary scanning modes. The images in each image set may correspond to the selected 105 plurality of defects of interest and nuisance data. The processor may collect 109 the one or more image sets from the additionally performed 107 scans. The one or more image sets may comprise sets of images of a defect of interest or nuisance data as recorded in one of the additionally performed 107 scans. Each image set may comprise a primary scanning mode image and one or more secondary scanning mode images corresponding to a selected defect of interest or nuisance data.

For example, an image set may contain an image of an area corresponding to the area of a defect of interest located using the primary scanning mode. The area for each image in an image set may be the same size, for example 32×32 pixels. In other embodiments, the area for each image in an image set may be of varying sizes Images in an image set may contain image data relating to a defect of interest, nuisance data, or both. The defects of interest may be similar to each of the images in an image set. In other embodiments, the defects of interest may be different types of defects.

The method 100 may further comprise dividing 111 each collected 109 image set into a first image subset and the second image subset. The processor may automatically divide 111 each collected 109 image set. The processor may divide 111 the image set into two equal subsets. In some embodiments, the processor may divide 111 the image set into a larger subset and a smaller subset. In other embodiments, the processor may divide 111 each collected 109 image set in the same way, for example, by grouping images representing the same area of the wafer into the same subsets across each image set. In other embodiments, the division 111 may be randomized. In some embodiments, multiple image subsets may be created from a single image set. For example, three or more subsets may be created. In another embodiment, multiple versions of the first and second subsets may be created.

In one embodiment, the division 111 may be performed on a pair-by-pair basis. For example, let $P^1$ comprise one or more images related to the primary scanning mode and $S^1 \ldots S^N$ each comprise one or more images related to the $N^{th}$ scanning mode. The collected 109 image sets may be divided 111 into sets comprising $P^1S^1, P^1S^2, \ldots, P^1S^N$. In another embodiment, the division 111 may be performed on a multiple-pair basis. For example, the collected 109 image sets may be divided 111 into sets comprising $P^1S^1S^2S^3$, $P^1S^4S^5S^6$, $P^1S^2S^4S^6$, $P^1S^1S^3S^5$, etc.

The method 100 may further comprise training 113, using the processor, for each secondary scanning mode, a CNN. The training 113 may be performed using the corresponding first image subset. In other embodiments, the training 113 may be performed using the corresponding second image subset. Each CNN may be trained 113 for each pair of primary scanning mode and one secondary scanning mode and/or primary scanning mode with many secondary scanning modes.

A CNN is a type of feed-forward artificial neural network in which the connectivity pattern between its neurons (i.e., pixel clusters) is inspired by the organization of the animal visual cortex. Individual cortical neurons respond to stimuli in a restricted region of space known as the receptive field. The receptive fields of different neurons partially overlap such that they tile the visual field. The response of an individual neuron to stimuli within its receptive field can be approximated mathematically by a convolution operation.

CNNs may comprise of multiple layers of receptive fields. These are small neuron collections which process portions of the input image or images. The outputs of these collections are then tiled so that their input regions overlap, to obtain a better representation of the original image. This may be repeated for every such layer. Tiling allows CNNs to tolerate translation of the input image. CNN may have a 3D volumes of neurons. The layers of a CNN may have neurons arranged in three dimensions: width, height and depth. The neurons inside a layer are only connected to a small region of the layer before it, called a receptive field. Distinct types of layers, both locally and completely connected, are stacked to form a CNN architecture. CNNs exploit spatially local correlation by enforcing a local connectivity pattern between neurons of adjacent layers. The architecture thus ensures that the learnt filters produce the strongest response to a spatially local input pattern. Stacking many such layers leads to non-linear filters that become increasingly global (i.e., responsive to a larger region of pixel space). This allows the network to first create good representations of small parts of the input, then assemble representations of larger areas from them. In CNNs, each filter is replicated across the entire visual field. These replicated units share the same parameterization (weight vector and bias) and form a feature map. This means that all the neurons in a given convolutional layer detect exactly the same feature. Replicating units in this way allows for features to be detected regardless of their position in the visual field, thus constituting the property of translation invariance.

Together, these properties allow convolutional neural networks to achieve better generalization on vision problems. Weight sharing also helps by dramatically reducing the number of free parameters being learnt, thus lowering the memory requirements for running the network. Decreasing the memory footprint allows the training of larger, more powerful networks. CNNs may include local or global pooling layers, which combine the outputs of neuron clusters. Pooling layers may also consist of various combinations of convolutional and fully connected layers, with pointwise nonlinearity applied at the end of or after each layer. A convolution operation on small regions of input is introduced to reduce the number of free parameters and improve generalization. One advantage of convolutional networks is the use of shared weight in convolutional layers, which means that the same filter (weights bank) is used for each pixel in the layer. This also reduces memory footprint and improves performance.

A CNN architecture may be formed by a stack of distinct layers that transform the input volume into an output volume (e.g., holding class scores) through a differentiable function. A few distinct types of layers may be used. The convolutional layer has a variety of parameters that consist of a set of learnable filters (or kernels), which have a small receptive field, but extend through the full depth of the input volume. During the forward pass, each filter may be convolved across the width and height of the input volume, computing the dot product between the entries of the filter and the input and producing a 2-dimensional activation map of that filter. As a result, the network learns filters that activate when they see some specific type of feature at some spatial position in the input. By stacking the activation maps for all filters along the depth dimension, a full output volume of the convolution layer is formed. Every entry in the output volume can thus also be interpreted as an output of a neuron that looks at a small region in the input and shares parameters with neurons in the same activation map.

When dealing with high-dimensional inputs such as images, it may be impractical to connect neurons to all neurons in the previous volume because such a network architecture does not take the spatial structure of the data into account. CNNs may exploit spatially local correlation by enforcing a local connectivity pattern between neurons of adjacent layers. For example, each neuron is connected to only a small region of the input volume. The extent of this connectivity is a hyperparameter called the receptive field of the neuron. The connections may be local in space (along width and height), but always extend along the entire depth of the input volume. Such an architecture ensures that the learnt filters produce the strongest response to a spatially local input pattern. In one embodiment, training 113 the CNN includes using transfer learning to create hyperparameters for each CNN. Transfer learning may include training a CNN on a very large dataset and then use the trained CNN weights either as an initialization or a fixed feature extractor for the task of interest.

Three hyperparameters control the size of the output volume of the convolutional layer: the depth, stride and zero-padding. Depth of the output volume controls the number of neurons in the layer that connect to the same region of the input volume. All of these neurons will learn to activate for different features in the input. For example, if the first CNN Layer takes the raw image as input, then different neurons along the depth dimension may activate in the presence of various oriented edges, or blobs of color. Stride controls how depth columns around the spatial dimensions (width and height) are allocated. When the stride is 1, a new depth column of neurons is allocated to spatial positions only 1 spatial unit apart. This leads to heavily overlapping receptive fields between the columns, and also to large output volumes. Conversely, if higher strides are used then the receptive fields will overlap less and the resulting output volume will have smaller dimensions spatially. Sometimes it is convenient to pad the input with zeros on the border of the input volume. The size of this zero-padding is a third hyperparameter. Zero padding provides control of the output volume spatial size. In particular, sometimes it is desirable to exactly preserve the spatial size of the input volume.

In some embodiments, a parameter sharing scheme may be used in layers to control the number of free parameters. If one patch feature is useful to compute at some spatial position, then it may also be useful to compute at a different position. In other words, denoting a single 2-dimensional slice of depth as a depth slice, neurons in each depth slice may be constrained to use the same weights and bias.

Since all neurons in a single depth slice may share the same parametrization, then the forward pass in each depth slice of the layer can be computed as a convolution of the neuron's weights with the input volume. Therefore, it is common to refer to the sets of weights as a filter (or a kernel), which is convolved with the input. The result of this convolution is an activation map, and the set of activation maps for each different filter are stacked together along the depth dimension to produce the output volume.

Sometimes, parameter sharing may not be effective, for example, when the input images to a CNN have some specific centered structure, in which completely different features are expected to be learned on different spatial locations.

Another important concept of CNNs is pooling, which is a form of non-linear down-sampling. There are several non-linear functions to implement pooling among which max pooling is one. Max pooling partitions the input image into a set of non-overlapping rectangles and, for each such sub-region, outputs the maximum. Once a feature has been found, its exact location may not be as important as its rough location relative to other features. The function of the pooling layer may be to progressively reduce the spatial size of the representation to reduce the amount of parameters and computation in the network, and hence to also control overfitting. A pooling layer may be positioned in-between successive cony layers in a CNN architecture.

Another layer in a CNN may be a ReLU (Rectified Linear Units) layer. This is a layer of neurons that applies a non-saturating activation function. A ReLU layer may increase the nonlinear properties of the decision function and of the overall network without affecting the receptive fields of the convolution layer.

Finally, after several convolutional and/or max pooling layers, the high-level reasoning in the neural network is completed via fully connected layers. Neurons in a fully connected layer have full connections to all activations in the previous layer. Their activations can hence be computed with a matrix multiplication followed by a bias offset.

In some embodiments, dropout techniques may be utilized to prevent overfitting. As referred to herein, dropout techniques are a regularization technique for reducing overfitting in neural networks by preventing complex co-adaptations on training data. The term "dropout" refers to dropping out units (both hidden and visible) in a neural network. For example, at each training stage, individual nodes may be either "dropped out" of the CNN with probability 1−p or kept with probability p, so that a reduced CNN remains. In some embodiments, incoming and outgoing edges to a dropped-out node may also be removed. Only the reduced CNN is trained. Removed nodes may then be reinserted into the network with their original weights.

In training stages, the probability a hidden node will be retained (i.e. not dropped) may be approximately 0.5. For input nodes, the retention probability may be higher. By avoiding training all nodes on all training data, dropout decreases overfitting in CNNs and significantly improves the speed of training.

Many different types of CNNs may be used in embodiments of the present disclosure. Different CNNs may be used based on certain scanning modes or circumstances. The configuration of a CNN may change based on the wafer, image data acquisition subsystem, or predetermined parameters.

The method 100 may further comprise determining 115 an ideal secondary scanning mode. The ideal secondary scanning mode may be determined 115 by applying each CNN to the corresponding second image subset. An ideal secondary scanning mode may be determined 115 by comparing the outputs of each CNN. For example, an ideal secondary scanning mode may be associated with the CNN having the highest signal-to-noise ratio in its output. In another example, an ideal secondary scanning mode may be associated with the CNN having the highest defect of interest identification rate. In another example, an ideal secondary scanning mode may be associated with the CNN having the lowest amount of output nuisance data. In another embodiment, the CNN is evaluated based on the separation between the plurality of defects of interest and nuisance data.

The method 100 may further comprise performing 117 a final hot scan using the ideal secondary scanning mode. The final hot scan may be performed 117 using the same image data acquisition subsystem or a different image data acquisition subsystem. The final hot scan may be performed 117 at a higher speed or using parameters that cause a lower signal-to-noise ratio. In some embodiments, only data corresponding to the defect of interest locations may be scanned. In other embodiments, the entire wafer may be scanned.

The method 100 may further comprise classifying 119 defects from the final hot scan by using the CNN corresponding to the ideal secondary scanning mode to filter out nuisance data in the final hot scan. The defects may be classified 119 based on type, location, severity, or any other objective parameter.

Figure 4:
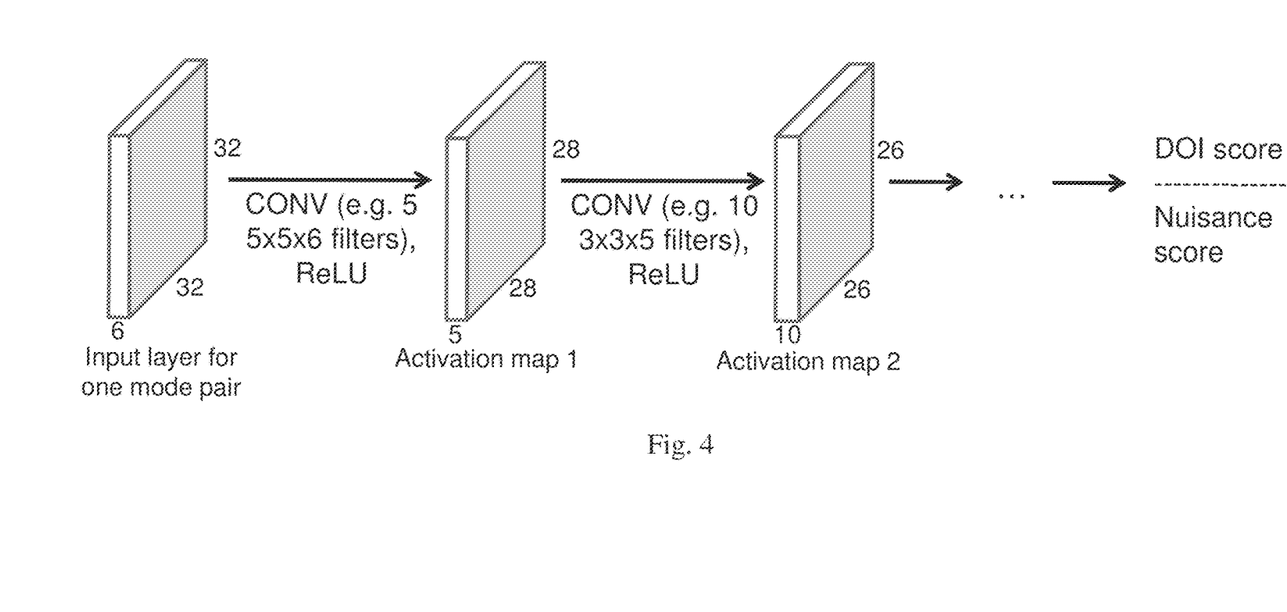
FIG. 4 is a diagram illustrating one potential convolutional neural network (CNN) structure.

Although many types of CNNs may be used, an exemplary CNN compatible with the presently disclosed method may be as shown in FIG. 4. The input layer for one scanning mode may be configured to receive six images. The six images may comprise a test image, a reference image, and a difference image for the primary scanning mode and a test image, a reference image, and a difference image for one of the secondary scanning modes. The images may represent defects of interest and/or nuisance data. The images may be 32 ×32 in size. The input layer may be convolved, for example, using five 5 ×5 ×6 filters. An optional ReLU layer may be included during or after the five convolutions. The result of these convolutions is the first activation map. The first activation map may be 5 ×28 ×28. Convolutions may be performed on the first activation map, for example, convolutions using ten 3 ×3 ×6 filters. An optional ReLU layer may be included during or after the ten convolutions. The resulting layer may be a second activation map. The second activation map may be 10 ×26 ×26. Additional convolutions may be performed until a fully connected layer has been established. Zero padding and pooling layers can be used as needed. Alternatively, a design clip may be added as an input resulting in a 32 ×32 ×7 input layer stack.

Another embodiment of the present disclosure can be described as a system for classifying defects. The system may comprise an image data acquisition subsystem and a processor in electronic communication with the image data acquisition subsystem.

The processor may be configured to identify a primary scanning mode; instruct the image data acquisition subsystem to return a first hot scan using the identified primary scanning mode; identify a plurality of defects of interest and nuisance data in the returned first hot scan; instruct the image data acquisition subsystem to return one or more additional scans using one or more secondary scanning modes; collect one or more image sets for each of the one or more secondary scanning modes, the images in each image set corresponding to the identified plurality of defects of interest and nuisance data; divide each collected image set into a first image subset and a second image subset; train, for each secondary scanning mode, a CNN with the corresponding first image subset; determine an ideal secondary scanning mode by applying each CNN to the corresponding second image subset; instruct the image data acquisition subsystem to return a final hot scan using the ideal secondary scanning mode; and classify defects from the final hot scan by using the CNN corresponding to the ideal secondary scanning mode to filter out nuisance data in the final hot scan. In one embodiments, the system may further comprise a database in electronic communication with the processor and the image data acquisition subsystem. The database may be configured to store classified defects from the final hot scan or CNNs.

In one embodiment an image of a reticle generated by a reticle inspection system is used as image data in the image data space. In this manner an image or a reticle generated by a reticle inspection system may be used as a substitute for image data. The image of the reticle used in this embodiment may include any suitable image of the reticle generated in any suitable manner by any reticle inspection system known in the art. For example the image of the reticle may be a high magnification optical or electron beam image of the reticle acquired by a high magnification optical reticle inspection system or an electron beam based reticle inspection system respectively. Alternatively the image of the reticle may be an aerial image of the reticle acquired by an aerial imaging reticle inspection system.

In one embodiment, an inspection system is used to collect image data. For example, the optical and electron beam output acquisition subsystems described herein may be configured as inspection systems. In another embodiment, the image data acquisition subsystem is a defect review system. For example, the optical and electron beam output acquisition subsystems described herein may be configured as defect review systems. In a further embodiment, the image data acquisition subsystem is a metrology system. For example, the optical and electron beam output acquisition subsystems described herein may be configured as metrology systems. In particular, the embodiments of the output acquisition subsystems described herein and shown in FIG. 2 may be modified in one or more parameters to provide different imaging capability depending on the application for which they will be used. In one such example, the image data acquisition subsystem shown in FIG. 2 may be configured to have a higher resolution if it is to be used for defect review or metrology rather than for inspection. In other words, the embodiments of the image data acquisition subsystem shown in FIG. 2 describe some general and various configurations for an image data acquisition subsystem that can be tailored in a number of manners that will be obvious to one skilled in the art to produce output acquisition subsystems having different imaging capabilities that are more or less suitable for different applications.

The systems and methods of the present disclosure may utilize output acquisition subsystems, defect review output acquisition subsystems, and metrology image data acquisition subsystems that are configured for inspection, defect review, and metrology of specimens such as wafers and reticles. For example, the embodiments described herein may be configured for using both scanning electron microscopy (SEM) and optical images for the purposes of mask inspection, wafer inspection, and wafer metrology. In particular, the embodiments described herein may be installed on a computer node or computer cluster that is a component of or coupled to an image data acquisition subsystem such as a broadband plasma inspector, an electron beam inspector or defect review tool, a mask inspector, a virtual inspector, etc. In this manner, the embodiments described herein may generate output that can be used for a variety of applications that include, but are not limited to, wafer inspection, mask inspection, electron beam inspection and review, metrology, etc. The characteristics of the output acquisition subsystems shown in FIG. 2 can be modified as described above based on the specimen for which it will generate actual output.

Figure 2:
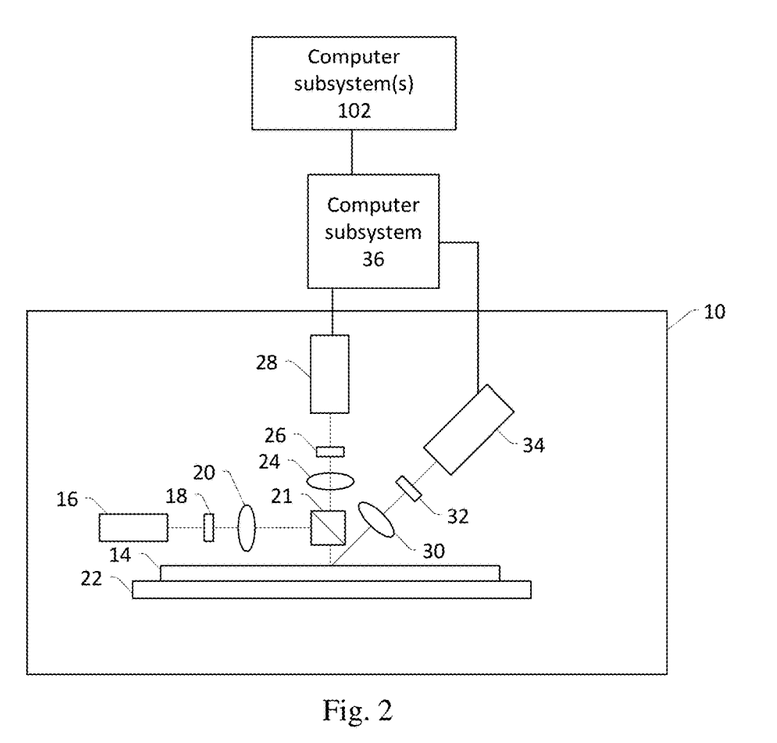
FIG. 2 is a system drawing of a system used in conjunction with one embodiment of the present disclosure.

Such a subsystem includes an image data acquisition subsystem that includes at least an energy source and a detector. The energy source is configured to generate energy that is directed to a wafer. The detector is configured to detect energy from the wafer and to generate output responsive to the detected energy.

In one embodiment, the energy directed to the wafer includes light, and the energy detected from the wafer includes light. For example, in the embodiment of the system shown in FIG. 2, image data acquisition subsystem 10 includes an illumination subsystem configured to direct light to wafer 14. The illumination subsystem includes at least one light source. For example, as shown in FIG. 2, the illumination subsystem includes light source 16. In one embodiment, the illumination subsystem is configured to direct the light to the wafer at one or more angles of incidence, which may include one or more oblique angles and/or one or more normal angles. For example, as shown in FIG. 2, light from light source 16 is directed through optical element 18 and then lens 20 to beam splitter 21, which directs the light to wafer 14 at a normal angle of incidence. The angle of incidence may include any suitable angle of incidence, which may vary depending on, for instance, characteristics of the wafer.

The illumination subsystem may be configured to direct the light to the wafer at different angles of incidence at different times. For example, the image data acquisition subsystem may be configured to alter one or more characteristics of one or more elements of the illumination subsystem such that the light can be directed to the wafer at an angle of incidence that is different than that shown in FIG. 2. In one such example, the image data acquisition subsystem may be configured to move light source 16, optical element 18, and lens 20 such that the light is directed to the wafer at a different angle of incidence.

In some instances, the image data acquisition subsystem may be configured to direct light to the wafer at more than one angle of incidence at the same time. For example, the illumination subsystem may include more than one illumination channel, one of the illumination channels may include light source 16, optical element 18, and lens 20 as shown in FIG. 2 and another of the illumination channels (not shown) may include similar elements, which may be configured differently or the same, or may include at least a light source and possibly one or more other components such as those described further herein. If such light is directed to the wafer at the same time as the other light, one or more characteristics (e.g., wavelength, polarization, etc.) of the light directed to the wafer at different angles of incidence may be different such that light resulting from illumination of the wafer at the different angles of incidence can be discriminated from each other at the detector(s).

In another instance, the illumination subsystem may include only one light source (e.g., source 16 shown in FIG. 2) and light from the light source may be separated into different optical paths (e.g., based on wavelength, polarization, etc.) by one or more optical elements (not shown) of the illumination subsystem. Light in each of the different optical paths may then be directed to the wafer. Multiple illumination channels may be configured to direct light to the wafer at the same time or at different times (e.g., when different illumination channels are used to sequentially illuminate the wafer). In another instance, the same illumination channel may be configured to direct light to the wafer with different characteristics at different times. For example, in some instances, optical element 18 may be configured as a spectral filter and the properties of the spectral filter can be changed in a variety of different ways (e.g., by swapping out the spectral filter) such that different wavelengths of light can be directed to the wafer at different times. The illumination subsystem may have any other suitable configuration known in the art for directing the light having different or the same characteristics to the wafer at different or the same angles of incidence sequentially or simultaneously.

In one embodiment, light source 16 may include a broadband plasma (BBP) light source. In this manner, the light generated by the light source and directed to the wafer may include broadband light. However, the light source may include any other suitable light source such as a laser. The laser may include any suitable laser known in the art and may be configured to generate light at any suitable wavelength or wavelengths known in the art. In addition, the laser may be configured to generate light that is monochromatic or nearly-monochromatic. In this manner, the laser may be a narrowband laser. The light source may also include a polychromatic light source that generates light at multiple discrete wavelengths or wavebands.

Light from optical element 18 may be focused to beam splitter 21 by lens 20. Although lens 20 is shown in FIG. 2 as a single refractive optical element, it is to be understood that, in practice, lens 20 may include a number of refractive and/or reflective optical elements that in combination focus the light from the optical element to the wafer. The illumination subsystem shown in FIG. 2 and described herein may include any other suitable optical elements (not shown). Examples of such optical elements include, but are not limited to, polarizing component(s), spectral filter(s), spatial filter(s), reflective optical element(s), apodizer(s), beam splitter(s), aperture(s), and the like, which may include any such suitable optical elements known in the art. In addition, the system may be configured to alter one or more of the elements of the illumination subsystem based on the type of illumination to be used for output acquisition.

The image data acquisition subsystem may also include a scanning subsystem configured to cause the light to be scanned over the wafer. For example, the image data acquisition subsystem may include stage 22 on which wafer 14 is disposed during output acquisition. The scanning subsystem may include any suitable mechanical and/or robotic assembly (that includes stage 22) that can be configured to move the wafer such that the light can be scanned over the wafer. In addition, or alternatively, the image data acquisition subsystem may be configured such that one or more optical elements of the image data acquisition subsystem perform some scanning of the light over the wafer. The light may be scanned over the wafer in any suitable fashion.

The image data acquisition subsystem further includes one or more detection channels. At least one of the one or more detection channels includes a detector configured to detect light from the wafer due to illumination of the wafer by the image data acquisition subsystem and to generate output responsive to the detected light. For example, the image data acquisition subsystem shown in FIG. 2 includes two detection channels, one formed by collector 24, element 26, and detector 28 and another formed by collector 30, element 32, and detector 34. As shown in FIG. 2, the two detection channels are configured to collect and detect light at different angles of collection. In some instances, one detection channel is configured to detect specularly reflected light, and the other detection channel is configured to detect light that is not specularly reflected (e.g., scattered, diffracted, etc.) from the wafer. However, two or more of the detection channels may be configured to detect the same type of light from the wafer (e.g., specularly reflected light). Although FIG. 2 shows an embodiment of the image data acquisition subsystem that includes two detection channels, the image data acquisition subsystem may include a different number of detection channels (e.g., only one detection channel or two or more detection channels). Although each of the collectors are shown in FIG. 2 as single refractive optical elements, it is to be understood that each of the collectors may include one or more refractive optical element(s) and/or one or more reflective optical element(s).

The one or more detection channels may include any suitable detectors known in the art. For example, the detectors may include photo-multiplier tubes (PMTs), charge coupled devices (CCDs), and time delay integration (TDI) cameras. The detectors may also include any other suitable detectors known in the art. The detectors may also include non-imaging detectors or imaging detectors. In this manner, if the detectors are non-imaging detectors, each of the detectors may be configured to detect certain characteristics of the scattered light such as intensity but may not be configured to detect such characteristics as a function of position within the imaging plane. As such, the output that is generated by each of the detectors included in each of the detection channels of the image data acquisition subsystem may be signals or data, but not image signals or image data. In such instances, a computer subsystem such as computer subsystem 36 of the system may be configured to generate images of the wafer from the non-imaging output of the detectors. However, in other instances, the detectors may be configured as imaging detectors that are configured to generate imaging signals or image data. Therefore, the system may be configured to generate the images described herein in a number of ways.

It is noted that FIG. 2 is provided herein to generally illustrate a configuration of an image data acquisition subsystem that may be included in the system embodiments described herein. Obviously, the image data acquisition subsystem configuration described herein may be altered to optimize the performance of the system as is normally performed when designing a commercial system. In addition, the systems described herein may be implemented using an existing output acquisition system (e.g., by adding functionality described herein to an existing output acquisition system) such as tools that are commercially available from KLA-Tencor. For some such systems, the methods described herein may be provided as optional functionality of the output acquisition system (e.g., in addition to other functionality of the output acquisition system). Alternatively, the system described herein may be designed "from scratch" to provide a completely new system.

Computer subsystem 36 of the system may be coupled to the detectors of the image data acquisition subsystem in any suitable manner (e.g., via one or more transmission media, which may include "wired" and/or "wireless" transmission media) such that the computer subsystem can receive the output generated by the detectors during scanning of the wafer. Computer subsystem 36 may be configured to perform a number of functions using the output of the detectors as described herein and any other functions described further herein. This computer subsystem may be further configured as described herein.

This computer subsystem (as well as other computer subsystems described herein) may also be referred to herein as computer system(s). Each of the computer subsystem(s) or system(s) described herein may take various forms, including a personal computer system, image computer, mainframe computer system, workstation, network appliance, Internet appliance, or other device. In general, the term "computer system" may be broadly defined to encompass any device having one or more processors, which executes instructions from a memory medium. The computer subsystem(s) or system(s) may also include any suitable processor known in the art such as a parallel processor. In addition, the computer subsystem(s) or system(s) may include a computer platform with high speed processing and software, either as a standalone or a networked tool.

If the system includes more than one computer subsystem, then the different computer subsystems may be coupled to each other such that images, data, information, instructions, etc. can be sent between the computer subsystems as described further herein. For example, computer subsystem 36 may be coupled to computer subsystem(s) 102 by any suitable transmission media, which may include any suitable wired and/or wireless transmission media known in the art. Two or more of such computer subsystems may also be effectively coupled by a shared computer-readable storage medium (not shown).

Figure 3:
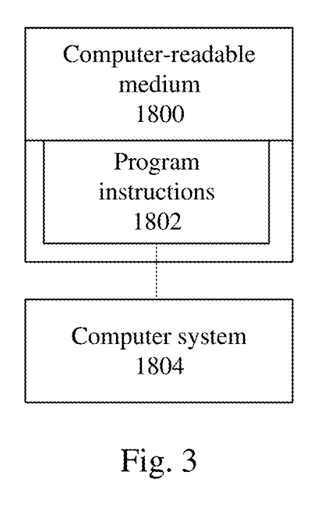
FIG. 3 is a diagram showing a non-transitory computer-readable medium storing program instructions executable on a computer system for performing a computer-implemented method of the present disclosure.

An additional embodiment relates to a non-transitory computer-readable medium storing program instructions executable on a computer system for performing a computer-implemented method for mode selection and image fusion. One such embodiment is shown in FIG. 3. In particular, as shown in FIG. 3, non-transitory computer-readable medium 1800 includes program instructions 1802 executable on computer system 1804. The computer-implemented method may include any step(s) of any method(s) described herein.

Program instructions 1802 implementing methods such as those described herein may be stored on computer-readable medium 1800. The computer-readable medium may be a storage medium such as a magnetic or optical disk, a magnetic tape, or any other suitable non-transitory computer-readable medium known in the art.

The program instructions may be implemented in any of various ways, including procedure-based techniques, component-based techniques, and/or object-oriented techniques, among others. For example, the program instructions may be implemented using ActiveX controls, C++ objects, JavaBeans, Microsoft Foundation Classes ("MFC"), SSE (Streaming SIMD Extension) or other technologies or methodologies, as desired.

Computer system 1804 may be configured according to any of the embodiments described herein.

Although the present disclosure has been described with respect to one or more particular embodiments, it will be understood that other embodiments of the present disclosure may be made without departing from the spirit and scope of the present disclosure. Hence, the present disclosure is deemed limited only by the appended claims and the reasonable interpretation thereof.

What is claimed is:
1. A method for classifying defects comprising:
identifying, using a processor, a primary scanning mode;
performing, using an image data acquisition subsystem, a first hot scan using the identified primary scanning mode;
selecting, using the processor, a plurality of defects of interest and nuisance data in the first hot scan;
performing, using the image data acquisition subsystem, one or more additional scans using one or more secondary scanning modes;
collecting, using the processor, one or more image sets, each image set comprising a primary scanning mode image and one or more secondary scanning mode images corresponding to a selected defect of interest or nuisance data;
dividing, using the processor, each collected image set into a first image subset and a second image subset;

training, using the processor, for each pair of primary scanning mode and secondary scanning mode, a convolutional neural network (CNN) with the corresponding first image subset;
determining an ideal secondary scanning mode, using the processor, by applying each CNN to the corresponding second image subset;
performing, using the image data acquisition subsystem, a final hot scan using the ideal secondary scanning mode; and
classifying, using the processor, defects from the final hot scan by using the CNN corresponding to the ideal secondary scanning mode to filter out nuisance data in the final hot scan.

2. The method of claim 1, wherein the primary scanning mode is identified by running a hot scan to detect a defect.

3. The method of claim 1, wherein the one or more secondary scanning modes deviate from the primary scanning mode based on focus offset.

4. The method of claim 1, wherein the one or more secondary scanning modes deviate from the primary scanning mode based on aperture.

5. The method of claim 1, wherein the one or more secondary scanning modes deviate from the primary scanning mode based on spectrum.

6. The method of claim 1, wherein the one or more secondary scanning modes deviate from the primary scanning mode based on polarization.

7. The method of claim 1, wherein the step of training the CNN includes using transfer learning to create hyperparameters for each CNN.

8. The method of claim 1, wherein each CNN is evaluated based on a separation between the plurality of defects of interest and nuisance data.

9. The method of claim 1, wherein each additional scan uses a different secondary scanning mode.

10. The method of claim 1, wherein input to the CNN is six images per selected defect of interest and nuisance data.

11. The method of claim 10, wherein the images are 32×32 pixels in size.

12. The method of claim 10, wherein the six images comprise a test image, a reference image, a difference image for the primary scanning mode and a test image, a reference image, and a difference image for one of the secondary scanning modes.

13. The method of claim 1, wherein input images are processed through one or more rectified linear unit layers.

14. The method of claim 13, wherein the rectified linear unit layer utilizes one or more filters.

15. The method of claim 13, wherein an end result is a fully connected layer.

16. The method of claim 13, wherein one or more pooling layers are utilized.

17. A system for classifying defects comprising:
an image data acquisition subsystem; and
a processor in electronic communication with the image data acquisition subsystem, the processor configured to:
identify a primary scanning mode;
instruct the image data acquisition subsystem to return a first hot scan using the identified primary scanning mode;
identify a plurality of defects of interest and nuisance data in the returned first hot scan;
instruct the image data acquisition subsystem to return one or more scans using one or more secondary scanning modes;
collect one or more image sets, each image set comprising a primary scanning mode image and one or more secondary scanning mode images corresponding to a selected defect of interest or nuisance data;
divide each collected image set into a first image subset and a second image subset;
train, for each pair of primary scanning mode and secondary scanning mode, a convolutional neural network (CNN) with the corresponding first image subset;
determine an ideal secondary scanning mode by applying each CNN to the corresponding second image subset;
instruct the image data acquisition subsystem to return a final hot scan using the ideal secondary scanning mode; and
classify defects from the final hot scan by using the CNN corresponding to the ideal secondary scanning mode to filter out nuisance data in the final hot scan.

18. The system of claim 17 further comprising a database in electronic communication with the processor and the image data acquisition subsystem, the database configured to store classified defects from the final hot scan.

19. The system of claim 18, wherein the database is also configured to store one or more CNNs.

* * * * *